United States Patent [19]

Yeh

[11] Patent Number: 5,378,830

[45] Date of Patent: Jan. 3, 1995

[54] AMPHOTERIC POLYSACCHARIDE COMPOSITIONS

[75] Inventor: Michael H. Yeh, Hamilton, N.J.

[73] Assignee: Rhone-Poulenc Specialty Chemicals Co., Cranbury, N.J.

[21] Appl. No.: 115,180

[22] Filed: Sep. 1, 1993

[51] Int. Cl.$^6$ .................. C07H 11/00; C07H 13/12
[52] U.S. Cl. ..................................... 536/118; 536/123
[58] Field of Search ............................. 536/123, 118

[56] References Cited

U.S. PATENT DOCUMENTS

| | | |
|---|---|---|
| 3,467,647 | 9/1969 | Benninga . |
| 3,912,713 | 10/1975 | Boonstra et al. . |
| 4,031,305 | 6/1977 | Demartino ..................... 536/114 |
| 4,057,509 | 11/1977 | Costanza et al. ................ 252/316 |
| 4,264,322 | 4/1981 | Lewis et al. . |
| 4,403,360 | 9/1983 | Finney et al. . |
| 4,454,617 | 6/1984 | Moates et al. . |
| 5,132,284 | 7/1992 | Tsai ................................. 507/110 |
| 5,132,285 | 7/1992 | Tsai ................................. 507/121 |

FOREIGN PATENT DOCUMENTS 2242401  3/1975  France .
1518731  6/1969  Germany .

OTHER PUBLICATIONS

Viscosity Behavior and Oil Recovery Properties of Interacting Polymers 1991 (Chapter 29) (pp. 447–465) Author: John K. Borchardt.

*Primary Examiner*—Nathan M. Nutter
*Attorney, Agent, or Firm*—Andrew M. Solomon

[57] ABSTRACT

A novel blend composition comprising one or more cationic polysaccharides and one or more anionic polysaccharides is provided. The blend is capable of producing enhanced viscosities when distributed in a solvent. The blend is suitable for use in foods, explosives, oil field chemicals, textile fibers, paper production, personal care products, agricultural chemicals and cosmetics.

21 Claims, No Drawings

AMPHOTERIC POLYSACCHARIDE COMPOSITIONS

BACKGROUND OF THE INVENTION

1. Field of the Invention

The present invention relates to a polysaccharide blend composition, preferably polygalactomannans which includes both cationic and anionic materials. More specifically, the blend composition includes a polysaccharide containing sulfonated anionic groups which are preferably derived from ethylenically unsaturated monomers including one or more sulfonate groups. The resulting compositions exhibit enhanced viscosities as compared to the viscosities obtained when using the cationic and anionic polysaccharides separately or as compared to the viscosity of using nonionic polysaccharides or other anionic/cationic polysaccharide blend combinations.

2. Technology Description

Natural and synthetic gums have been used as thickeners for foods, coatings, paints, explosive slurries, oil well fluids, cosmetics, and many other functional applications. One class of gums that have been widely used as suspending and viscosity agents are polygalactomannans. Polygalactomannans are polysaccharides composed principally of galactose and mannose units and are usually found in the endosperm of leguminous seeds such as guar, locust bean, honey locust, flame tree, and the like. In practice, to thicken a fluid the polygalactomannans may either be added by themselves, or with other viscosity modifiers such as other polygalactomannans, xanthan gum and the like.

U.S. Pat. No. 3,467,647 disclose polysaccharides containing both cationic and anionic substituents. Amongst the starting polysaccharides which are then modified according to this patent include starches, locust bean gum (carob gum) and guar gum. Cationic substituents include primary, secondary, or tertiary amino groups or quaternary ammonium, sulfonium or phosphinium groups. Suggested anionic substituents include carboxyl, sulfonate, sulfate or phosphate groups. Example 9 of this patent discloses guar gum as the polysaccharide, trimethylammoniumhydroxypropyl as the cationic groups, and phosphates as the anionic groups. The degree of substitution for each of these groups in this example is 0.05.

Similarly, DD 281966 discloses a gel former which has both cationic and anionic polymers and provides a synergistic increase in viscosity as compared to solutions which contain separate amounts of the polymers. The cationic polymer is preferably a poly(dimethyldiallylammonium chloride) containing pyrrolidinium units and the anionic polymer is preferably carboxymethylcellulose with a degree of substitution of 0.6–1.2.

U.S. Pat. Nos. 4,264,322; 4,403,360 and 4,454,617 disclose dye compositions for textile fibers. The compositions comprise an admixture of immiscible gel phases, wherein one gel phase is thickened with a cationic gelling agent and wherein a second gel phase, which is dispersed in the first gel phase, is thickened with an anionic gelling agent. Suggested cationic gelling agents for the first phase include cationic polygalactomannans containing quaternary ammonium ether substituents. Suggested anionic gelling agents for the second phase include hydrocolloids which have the same type of basic polymeric structure as the cationic gelling agents, except that in place of the cationic group there is substituted an anionic group such as a carboxylic acid, sulfonic acid, or sulfate.

A number of references disclose polygalactomannans containing different substituents. None of these references disclose or suggest that these substituted polygalactomannans be combined with other polygalactomannans to yield a superior viscosity modifying composition. For example, DE 1,518,731 discloses that galactomannans or glucomannans may be etherified with β-halogen ethane sulfonic acid or halogen methane sulfonic acids in the presence of base to yield compositions which can function as textile finishes, sizes and print thickeners.

U.S. Pat. No. 3,912,713 and FR 2,242,401 disclose guar gum derivatives and processes for preparing the derivatives. The derivatives are prepared by adding a substituent to guar gum splits in the presence of water, and typically, base. Amongst the substituents (derivatizing agents) suggested for use in these patents are haloalkylsulfonic acids, such as bromoethanesulfonic acid and chlorohydroxypropanesulfonic acid, epoxyalkyl sulfonic acids, such as epoxypropane sulfonic acid, and α,β-alkylene sulfonic acids, such as ethylene sulfonic acid. These compounds are suggested for use as thickening agents, stressing, sizing and finishing agents, protective colloids and as agents for stabilizing dispersions and emulsions.

U.S. Pat. No. 4,031,305 discloses sulfohydroxypropyl ethers of polygalactomannans having a degree of substitution between about 0.01 and 3. The ethers are prepared by contacting solid guar gum or locust bean gum with a 3-halo-2-hydroxypropanesulfonic acid or acid salt in the presence of base. The galactomannan ethers are alleged to be anionic in nature and are proposed for use in petroleum, textile, printing, paper, food and pharmaceutical industries.

U.S. Pat. No. 4,057,509 discloses the formation of an acidic gel by contacting a polygalactomannan with an allyl halide, followed by exposing the formed polygalactomannan allyl ether material to a stream of sulfur dioxide. The gels are suggested for use in oil well drilling mud compsitions and oil well fracturing compositions.

Borchardt, "Viscosity Behavior and Oil Recovery Properties of Interacting Polymers", *Water-Soluble Polymers*, pp. 446–465, 1991, (Chem. Abstracts CA115(16):16250p) discusses the use of certain polymer combinations which provide enhanced viscosities as compared to the viscosities of the individual polymers. Combinations mentioned include poly(styrene sulfonate) and either xanthan gum or hydroxyethyl cellulose, poly(vinyl sulfonate) and Xanthan gum, a quaternary-ammonium-salt modified guar and either hydroxypropyl guar or hydroxyethyl cellulose, and a sulfonated guar (D.S. of 0.10; chemical name not mentioned) and either hydroxyethyl cellulose or carboxymethylhydroxyethyl cellulose. These combinations are suggested for use in oil recovery.

U.S. Pat. Nos. 5,132,284 and 5,132,285 disclose neutrally charged polyamphoteric polysaccharide graft copolymers. The references suggest that guar gum or a derivative of guar gum may be used as the base polysaccharide and that the polymer chain includes grafted cationic and anionic substituents. These materials are suggested for use in oil field applications.

Despite the above, there still is a need for compositions which demonstrate enhanced viscosity behavior.

BRIEF SUMMARY OF THE INVENTION

In accordance with the present invention, a novel combination which demonstrates enhanced viscosity behavior than each of the starting polymers and which utilizes both ionic and molecular forces to achieve the enhanced viscosity behavior is provided. The novel combination comprises one or more cationic polysaccharides, preferably polygalactomannans and one or more anionic polysaccharides, preferably polygalactomannans, wherein at least one of the anionic polysaccharides includes one or more sulfonate groups.

One embodiment of the present invention comprises a blend composition comprising about 1 to about 99 parts of one or more cationic polysaccharides, preferably polygalactomannans having a degree of substitution of about 0.01 to about 3.00 and about 99 to about 1 parts of one or more anionic polysaccharides, preferably polygalactomannans having a degree of substitution of about 0.01 to about 3.00, wherein at least one of said anionic polysaccharides contains one or more sulfonate groups.

In particularly preferred embodiments, each of the cationic and anionic polygalactomannans selected are derived from guar gum or locust bean gum, and preferably guar gum. Further, the preferred degree of substitution for each of the polygalactomannan is between about 0.05 and about 2.0. In the case of the cationic polygalactomannans, the preferred cationic substituent comprises a quaternary ammonium group and in the case of the anionic polygalactomannans, the preferred anionic substituent includes one or more sulfonate groups and is derived from an ethylenically unsaturated monomer.

The blends are particularly effective as thickening agents. They may be used for a number of functional applications such as in foods, explosives, oil field chemicals, agricultural applications, cosmetics and the like.

Another embodiment of the present invention comprises a process for producing a viscous liquid or a gel. The process comprises the step of adding to a solvent, preferably water, 0.1 parts to about 2.0 parts per 100 parts viscous liquid or gel of a blend composition having a ratio of about 1 to about 99 parts of one or more cationic polysaccharides, preferably polygalactomannans having a degree of substitution of about 0.01 to about 3.00 and about 99 to about 1 parts of one or more anionic polysaccharides, preferably polygalactomannans having a degree of substitution of about 0.01 to about 3.00, wherein at least one of said anionic polysaccharides contains one or more sulfonate groups.

A third embodiment of the present invention comprises a food, explosive, oil field chemical, agricultural chemical, textile fiber or cosmetic including an amount of a blend composition having a ratio of about 1 to about 99 parts of one or more cationic polysaccharides, preferably polygalactomannans having a degree of substitution of about 0.01 to about 3.00 and about 1 to about 99 parts of one or more anionic polysaccharides, preferably polygalactomannans having a degree of substitution of about 0.01 to about 3.00, wherein at least one of said anionic polysaccharides contains one or more sulfonate groups.

Accordingly, it is an object of the present invention to provide a novel blend composition which comprises materials which, in combination, demonstrate a superior viscosity profile as compared to the materials individually.

It is another object of the present invention to provide a process for producing a viscous liquid or gel using a novel blend composition.

A further object of the present invention to provide a food, explosive, oil field chemical, agricultural chemical, paper chemical, personal care product, textile fiber or cosmetic which includes the novel blend composition.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

The present invention comprises an amphoteric polysaccharide blend composition comprising about 1 to about 99 parts of one or more cationic polysaccharides, preferably polygalactomannans having a degree of substitution of about 0.01 to about 3.00 and about 99 to about 1 parts of one or more anionic polysaccharides, preferably polygalactomannans having a degree of substitution of about 0.01 to about 3.00, wherein at least one of said anionic polysaccharides contains one or more sulfonate groups. In practice the materials may be mixed together in a dry state or, more preferably, each distributed in a fluid, preferably water, and each fluid is then mixed together.

The first component of the blend comprises one or more cationic polysaccharides, preferably polygalactomannans having a degree of substitution of between about 0.01 and about 3.0. Particularly preferred are cationic polygalactomannans having a degree of substitution of between about 0.05 and about 2.0, with a degree of substitution of between about 0.1 and about 1.0 being most preferred.

The polygalactomannans are polysaccharides composed principally of galactose and mannose units and are usually found in the endosperm of leguminous seeds, such as guar, locust bean, honey locust, flame tree, and the like. Guar flour, for example, is composed mostly of a galactomannan which is essentially a straight chain mannan with single membered galactose branches. The mannose units are linked in a 1-4-$\beta$-glycosidic linkage and the galactose branching takes place by means of a 1-16 linkage on alternate mannose units. The ratio of galactose to mannose in the guar polymer is, therefore, one to two. Guar gum has a molecular weight of about 1.5 million.

Locust bean gum is also a polygalactomannan gum of similar molecular structure in which the ratio of galactose to mannose is one to four. Guar and locust bean gum are the preferred sources of the polygalactomannans, principally because of the commercial availability thereof.

In use the polygalactomannan may be either in its natural state (i.e., pure guar gum or locust bean gum) or may be derivatized. Derivatized polygalactomannans include one or more non-ionic groups. Examples of such polygalactomannans include hydroxypropyl guar, hydroxyethyl guar, and the like. Such derivatized polygalactomannans are sold by Rhône-Poulenc Inc.

under the trade names Jaguar 8012, Jaguar 8060, Jaguar 8000, Jaguar HP-20 and Jaguar HP-23.

By the term "degree of substitution" as employed herein is meant the average substitution of cationic or anionic groups per anhydro sugar unit in the polygalactomannan gums. In guar gum, the basic unit of the polymer consists of two mannose units with a glycosidic linkage and a galactose unit attached to a hydroxyl group of one of the mannose units. On the average, each of the anhydro sugar units contains three available hydroxyl sites. A degree of substitution of three would mean that all of the available hydroxyl sites have been esterified with formate ester groups.

Alternative materials which may be selected as the starting material include starches, celluloses and xanthan gum. Examples of starches include both natural and modified starches, such as dextrinated, hydrolyzed, oxidized, cross-linked, alkylated, hydroxyalkylated, acetylated, or fractionated (e.g., amylose and amylopectin). The starch may be of any origin, for example, corn starch, wheat starch, potato starch, tapioca starch, sago starch, rice starch, waxy corn starch or high-amylose corn starch.

Examples of celluloses include hydroxyethyl cellulose, hydroxypropyl cellulose, and alkyl celluloses.

Illustrative cationic groups suitable for the practice of the present invention include quaternary ammonium groups. Typical of quaternary ammonium groups are tetramethylammonium chloride and bromide, benzyltrimethylammonium chloride and bromide, tetraethylammonium chloride and bromide, tetrabutylammonium chloride and bromide, methylpyridinium chloride and bromide, benzylpyridinium chloride and bromide, trimethyl-p-chlorobenzylammonium chloride and bromide, and the like, wherein each of the said groups is derivatized in the form of a radical which is substituted in a hydrocolloid gelling agent by means of an alkylene or oxyalkylene linkage.

The polymeric structure of suitable polygalactomannans including cationic groups include vinyl polymers and copolymers, ion exchange resins, polysaccharides, and the like. Illustrative of this class of hydrocolloids are polygalactomannan gums containing quaternary ammonium ether substituents as described in U.S. Pat. No. 4,031,307:

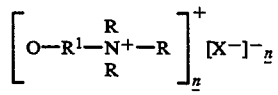

wherein R is an alkyl group containing between one and about six carbons atoms, $R^1$ is an alkyl group containing between one and about six carbon atoms, X is chlorine or bromine, and n is an integer which correlates with the degree of substitution of the quaternary ammonium ether substituents in a polygalactomannan gum cationic gelling agent. The said alkyl and alkylene group can contain other atoms such as oxygen, sulfur and halogen.

The cationic derivatives of guar gum or locust bean gum are prepared by contacting solid guar gum or locust bean gum with a haloalkyl-substituted quaternary ammonium compound and a stoichiometric excess of alkali metal hydroxide or ammonium hydroxide in a reaction medium comprising an aqueous solution of water-miscible solvent, at a temperature between about 10° C. and about 100° C. for a reaction period sufficient to achieve a degree of substitution by quaternary ammonium ether groups between about 0.01 and about 3.00.

The solid guar gum or other polygalactomannan which is etherified can be in the form of endosperm splits or in the form of finely divided powder which is derived from the endosperm splits. It is important that the polygalactomannan gum being etherified with quaternary ammonium groups remains as a solid phase in the reaction medium during the reaction period.

Further details on the synthesis of these polymers are provided in U.S. Pat. No. 4,031,307. To the extent necessary, this patent is incorporated by reference.

Examples of commercially available polygalactomannans having one or more substituted cationic quaternary ammonium groups include Jaguar C-13, Jaguar C-13S, Jaguar C-14, Jaguar C-17 and Jaguar C-14S, all sold by Rhône-Poulenc Inc.

Other cationic polygalactomannans having a degree of substitution between about 0.01 and 3.00 include those which contain other cationic groups such as acid salts of primary, secondary, and tertiary amines, sulfonium groups or phosphonium groups.

The other component of the inventive blend composition comprises one or more anionic polysaccharides, preferably polygalactomannans having a degree of substitution of about 0.01 to about 3.00, wherein at least one of said anionic polysaccharides contains one or more sulfonate groups. Particularly preferred are polygalactomannans having a degree of substitution of between about 0.05 and about 2.0, with a degree of substitution of between about 0.1 and about 1.0 being most preferred.

The anionic nature of this component is obtained by utilizing a substituent having one or more sulfonate groups. Particularly preferred as anionic substituents are those derived from ethlyenically unsaturated monomers containing one or more sulfonate groups. Examples of such monomers include the sodium salt of 2-acrylamido-2-methylpropane sulfonic acid and the sodium salt of 1-allyloxy-2-hydroxy-propylsulfonic acid. The former monomer is derived from 2-acrylamido-2-methylpropane sulfonic acid, which is commercially available from Lubrizol and sold under the trade name LZ 2401 and the later monomer is commercially available from Rhône-Poulenc Inc. and sold under the trade name Sipomer Cops I.

The formation of ether linkages between the sulfonated substituent and the polymer occurs by directly adding the substituent to the polygalactomannan, preferably in the presence of a solvent such as toluene. The reaction temperature generally is between about 10° C. and about 100° C. Reactivity of the polymer with the substituent may be aided by utilizing a small amount of an initiator. Examples of suitable initiators include ammonium persulfate. pH buffers, such as disodium phosphate, may also be optimally added.

Once dissolved in solution, and in particular, water, the sulfonated polygalactomannan may be crosslinked to provide a strong, thixotropic aqueous solution. Crosslinking of the solution is accomplished by adding aluminum acetate to the solution and adjusting the pH until the solution dramatically increases in viscosity. When using the ethylenically unsaturated monomers containing sulfonate groups, the pH is adjusted to above 8. This is in contrast to other anionic polygalactomannans such as carboxymethyl guar and carboxymethylhydroxypropyl guar, which tend to crosslink under acidic conditions (pH of 5 to 6).

When blended or otherwise mixed together, the ratio of cationic polysaccharide to anionic polysaccharide in this invention can be varied over a wide range. The preferred range is about 5 to about 95 parts by weight of cationic polymer to about 95 to about 5 parts by weight of anionic polymer, the total being 100 parts by weight. In use, the inventive compositions can effectively function as thickeners when added to a solvent, typically water. This typically comprises adding between about 0.1 and about 2.0 parts of the sulfonated anionic polymer the cationic polymer per 100 parts of viscous liquid or gel.

The amphoteric polysaccharide blend compositions are typically produced by combining solutions of both cationic and anionic polymers in respective amounts so that the positive and negative charges are equally balanced. The respective amounts of anionic and cationic solutions are added together based primarily upon the degree of substitution of each. For example, larger amounts of a low degree of substitution cationic polymer solution may be added to smaller amounts of a high degree of substitution anionic solution.

While in the preferred embodiment, the amounts of anionic and cationic solutions are added in relative amounts to produce a charge neutral solution, the amounts of each may be varied to yield solutions which have an overall positive or negative charge. Although not as enhanced as when producing a charge neutral solution, some synergistic viscosity increasing effect is achieved by unbalanced charged additions.

As an alternative to mixing separate aqueous solutions of the cationic and anionic polymers to obtain the inventive amphoteric blend, the cationic polysaccharide and the anionic polysachhardie may be mixed together in a dry state in the desired ratio and then added to the water as stated above. For easy handling and ready dispersibility, the gums should have a particle size of less then about 100 mesh. Other components, e.g., fillers, wetting agents, dispersants, bactericides, fungicides and the like can be mixed with the powdered blends of the invention if so desired.

The fact that interaction between different polygalactomannans can provide enhanced viscosities is known. What is surprising about this invention is that by utilizing cationic polysaccharides in combination with the specific sulfonated anionic polysaccharides a dual advantage is achieved. The first advantage is the enhanced viscosity brought about by the molecular interaction of the cationic polysaccharide with the anionic polysaccharide. The second advantage is the ionic interaction involved by using a cationic polysaccharide with the anionic sulfonated polysaccharide. By utilizing both the molecular and ionic forces, truly improved results are obtained as compared to blends which utilize nonionic polysaccharides.

The inventors have also discovered that it is critical that the anionic polymer used be a sulfonated one which has groups derived from ethylenically unsaturated monomers containing sulfonate groups. Not all mixtures of anionic and cationic polymers yield blend compositions which are superior to the individual reactant compositions. For example, when blending either carboxymethyl guar or carboxymethylhydroxypropyl guar, both anionic polygalactomannans, with Jaguar C-14, a cationic polygalactomannan manufactured by Rhône-Poulenc Inc., a lower solution viscosity is obtained than the viscosity obtained by using the cationic or anionic polygalactomannans separately. It is hypothesized that this is because of shrinkage of guar molecules caused by the strong reaction between the cationic functional group with the anionic carboxymethyl group. This dramatically reduces the hydrophilic nature of the polygalactomannan starting materials. By direct comparison, when using the sulfonated mildly anionic polymers according to the present invention in combination with cationic polygalactomannans, a marked increase in viscosity occurs. This indicates a syngergistic reaction between the two polygalactomannans such that they retain their hydrophilic properties.

The novel compositions, due to their thickening properties, have a wide number of possible uses. Amongst them are as suspending agents for various solids, such as in oil field chemicals, for use in dyeing textile fibers, for use in foods, for use in cosmetics and personal care products, for use with agricultural products, for use is explosives, for use in paper production and the like. Other uses will readily be appreciated by those skilled in the art.

The invention is described in greater detail by the following non-limiting examples.

EXAMPLE 1

174.4 parts of a 50% NaOH solution are dissolved in 373.8 parts of deionized water to make a 16% solution. The solution is cooled to room temperature. 452 parts of 2-acrylamido-2-methylpropane sulfonic acid monomer (AMPS) are added to the solution at between about 25 and about 30° C. After the AMPS has fully dissolved, the solution is cooled to 20° C. and the pH is adjusted to 9.1. The solvent is removed to yield sodium 2-acrylamido-2-methylpropane sulfonate monomer.

322 parts of guar gum are dispersed in 1200 parts of toluene in a nitrogen gas environment. A solution of 4 parts of ammonium persulfate and 3 parts of disodium phosphate in 50 parts water is added dropwise and the mixture is heated to about 60°–65° C. 382 parts of sodium 2-acrylamido-2-methylpropane sulfonate monomer solution (50% aqueous, pH=10.5) are added and the mixture is heated to 80° C. for 30 minutes and maintained at 70° C. for 3 hours. The mixture is then washed with 70% methanol for three times and with 99% methanol for one time. The yield of this product is 351 parts. The moisture content is 10% and the degree of substitution is about 0.42.

1 part of this material is dispersed in 100 parts water at 25° C. The viscosity measured two hours after hydration by a Brookfield Viscometer (RVT at 20 rpm) is 4500 cps. The same experiment is repeated except the solvent selected is an aqueous 2% KCl solution. The measured viscosity is 4000 cps.

To crosslink this material, a 0.48% solution of the experimental composition in water is prepared. The viscosity measured by a Brookfield Viscometer is 410 cps. 1 ml of a 5% aluminum acetate solution is added to the mixture. The addition causes the pH to lower to 4.8 while the viscosity remains essentially the same (420 cps). NaOH is added to the solution and the viscosity does not show a great increase until the pH exceeds 8. At a pH of 8.03, the viscosity dramatically increases to 17000 cps. At a pH of 8.7, the viscosity is about 35000 cps. The viscosity remains high throughout the basic pH range (pH between 8 and 11). The same experiment is repeated in an aqueous 2% KCl solution. Similar behavior is noted, with a dramatic increase in viscosity once the pH is greater than 8. (For example, at pH 7, the viscosity is 390 cps; at 7.5 the viscosity is 1300; at 8.03 the viscosity is 19000; and at 8.7, the viscosity is 37500).

EXAMPLE 2

322 parts of guar gum are suspended in 1300 parts of toluene in a nitrogen gas environment. A solution of 4 parts of ammonium persulfate and 3 parts of disodium phosphate in 50 parts water is added dropwise and the mixture is heated to about 60°–65° C. 372 parts of a sodium 2-acrylamido-2-methylpropane sulfonate monomer solution (pH adjusted to 10.0) are added and the resulting mixture is heated and maintained at 68°–70° C. for 2.5 hours. The mixture is then washed with 70% methanol for three times and with 99% methanol for one time. The yield of this product is 344 parts. The moisture content is 10%.

1 part of this material is dispersed in 100 parts water at 25° C. The viscosity measured two hours after hydration by a Brookfield Viscometer (RVT at 20 rpm) is 4800 cps.

EXAMPLE 3

322 parts of guar gum are suspended in 1300 parts of toluene in a nitrogen gas environment. A solution of 6 parts of ammonium persulfate and 4 parts of disodium phosphate in 80 parts water is added dropwise and the mixture is heated to about 60°–65° C. 267 parts of a sodium 1-allyloxy-2-hydroxypropyl sulfonate monomer solution (pH adjusted to 10.5) are added and the resulting mixture is heated and maintained at 65°–70° C. for 2.5 hours. The mixture is then washed with 70% methanol for three times and with 99% methanol for one time. The yield of this product is 338 parts. The moisture content is 10.9%.

1 part of this material is dispersed in 100 parts water at 25° C. The viscosity measured two hours after hydration by a Brookfield Viscometer (RVT at 20 rpm) is 4600 cps. 0.48 parts of this material is dispersed in 100 parts water at 25° C. The viscosity measured two hours after hydration by a Brookfield Viscometer (RVT at 20 rpm) is 166.

Comparative Example 4

A 1% solution of carboxymethyl guar (an anionic guar) is dissolved in water at 25° C. The viscosity measured two hours after hydration by a Brookfield Viscometer (RVT at 20 rpm) is 4000 cps. Similarly, a 1% solution of Jaguar C-14, a cationic guar is dissolved in water at 25° C. The viscosity measured two hours after hydration by a Brookfield Viscometer (RVT at 20 rpm) is 5600 cps. 1% aqueous solutions containing, respectively, 50 percent by weight carboxymethyl guar and 50 percent by weight Jaguar C-14 are mixed at 25° C. The viscosity measured by a Brookfield Viscometer (RVT at 20 rpm) is 2000 cps, a much lower viscosity than either of the individual viscosities of the anionic and cationic guars.

EXAMPLE 4

A 1% solution of the anionic sulfonated guar of Example 1 is dissolved in water at 25° C. The viscosity measured two hours after hydration by a Brookfield Viscometer (RVT at 20 rpm) is 4500 cps. Similarly, a 1% solution of Jaguar C-14 is dissolved in water at 25° C. The viscosity measured two hours after hydration by a Brookfield Viscometer (RVT at 20 rpm) is 5600 cps. 1% aqueous solutions containing, respectively, 50 percent by weight of the anionic sulfonated guar of Example 1 and 50 percent by weight C-14 are mixed at 25° C. The viscosity measured by a Brookfield Viscometer (RVT at 20 rpm) is 7600 cps, a much higher viscosity than either of the individual viscosities of the anionic and cationic guars.

EXAMPLE 5

1% aqueous solutions of the composition of Example 2 and of Jaguar C-14 are prepared and are mixed in various ratios. The viscosities are measured by a Brookfield Viscometer (RVT at 20 rpm) at 25° C. and the results are listed in Table 1.

TABLE 1

| Wt. % Example 2 | Wt. % C-14 | Viscosity |
| --- | --- | --- |
| 0 | 100 | 5100 cps |
| 25 | 75 | 6550 |
| 50 | 50 | 7200 |
| 75 | 25 | 6500 |
| 100 | 0 | 4800 |

COMPARATIVE TESTING

The following samples are used to compare the viscosities of 1% solutions of the samples in water at 25° C. two hours after hydration under different shear conditions:

Sample A—Example 2 Composition (100%)
Sample B—Jaguar C-14 (100 %)
Sample C—50:50 weight mixture of Sample A and Sample B
Sample D—Kelzan D (100%) (a commercial thickener sold by Kelco)
Sample E—Rhodigel (100%) (a commercial thickener (food grade xanthan gum) sold by Rhône-Poulenc Inc.).

The viscosities, in centipoises, and the shear rates, in rpms, are shown in Table 2.

TABLE 2

| RPM | 0.5 | 1 | 2.5 | 5 | 10 | 20 | 50 | 100 |
| --- | --- | --- | --- | --- | --- | --- | --- | --- |
| Sample A | 20000 | 17000 | 12400 | 10000 | 7100 | 4750 | 2600 | 1600 |
| Sample B | 26000 | 20000 | 14400 | 10000 | 6600 | 4150 | 2160 | 1260 |
| Sample C | 33000 | 30000 | 19200 | 13200 | 8600 | 5500 | 2880 | 1760 |
| Sample D | 35000 | 20500 | 10000 | 5700 | 3250 | 1875 | 880 | 510 |
| Sample E | 50000 | 27500 | 12800 | 7300 | 4050 | 2275 | 1050 | 590 |

The data of Table 2 demonstrates that the inventive compositions produce higher viscosities than the separate anionic and cationic guars at all shear rates and comparable viscosities to the commercial xanthan gums at low shear rates. At high shear rates, the inventive compositions yield higher viscosities than either of the commercial products.

TEMPERATURE STUDY

The viscosities of aqueous solutions of Sample C (1% concentration in water) are measured two hours after hydration at 70° F., 100° F., 120° F., 140° F., 150° F., 160° F., 180° F. and 200° F. at the shear rates a shown in Table 3.

TABLE 3

| RPM | 0.5 | 1 | 2.5 | 5 | 10 | 20 | 50 | 100 |
|---|---|---|---|---|---|---|---|---|
| 70° F. | 24000 | 20000 | 13200 | 9600 | 6700 | 4550 | 2620 | 1700 |
| 100° F. | 14000 | 12000 | 8400 | 6400 | 4600 | 3300 | 2000 | 1310 |
| 120° F. | 9000 | 6500 | 5400 | 4200 | 3150 | 2300 | 1420 | 950 |
| 140° F. | 5000 | 5000 | 3800 | 3000 | 2350 | 1775 | 1140 | 775 |
| 150° F. | 4000 | 3500 | 3000 | 2500 | 1950 | 1500 | 1000 | 690 |
| 160° F. | 4000 | 3500 | 2800 | 2300 | 1750 | 1425 | 950 | 650 |
| 180° F. | 3000 | 3000 | 2200 | 1800 | 1500 | 1200 | 820 | 575 |
| 200° F. | 2400 | 2200 | 1840 | 1560 | 1280 | 1130 | 736 | 560 |

Example 6

A solution of 2.4 parts ammonium persulfate and 3 parts disodium phosphate in 50 parts water is added to 322 parts of Rhodigel in 1300 parts toluene and the solution is heated to 70° C. 50 parts of a sodium 2-acrylamido-2-methylpropane sulfonate monomer solution are added and the reaction temperature is maintained at 65°-70° C. for two hours. The mixture is cooled, filtered and dehydrated with methanol. The yield is 370.8 parts, with a moisture content of 12%.

The following samples are used to compare the viscosities of 1% aqueous solutions at 25° C. two hours after hydration under different shear conditions:
Sample F—Rhodigel (100%) (xanthan gum)
Sample G—Example 7 Composition (100%)
Sample H—Jaguar C-14 (100 %) (cationic guar)
Sample I—Jaguar C-17 (100%) (cationic guar)
Sample J—50:50 weight mixture of Sample F and Sample H
Sample K—50:50 weight mixture of Sample G and Sample H
Sample L—50:50 weight mixture of Sample F and Sample I
Sample M—50:50 weight mixture of Sample G and Sample I.

The shear rates, in rpms, and the viscosities, in centipoises, are shown in Table 4.

TABLE 4

| RPM | 0.5 | 1 | 2.5 | 5 | 10 | 20 | 50 |
|---|---|---|---|---|---|---|---|
| Sample F | 50000 | 28500 | 13200 | 7600 | 4200 | 2400 | 1100 |
| Sample G | 68000 | 34000 | 17200 | 9200 | 5100 | 2800 | 1280 |
| Sample H | 32000 | 26000 | 18400 | 12800 | 8600 | 5500 | 2820 |
| Sample I | 10000 | 9000 | 6800 | 5200 | 3800 | 2650 | 1500 |
| Sample J | 57000 | 31500 | 14000 | 7800 | 4400 | 2500 | 1400 |
| Sample K | 68000 | 36000 | 16000 | 9200 | 5000 | 3300 | 2000 |
| Sample L | 148000 | 84000 | 36800 | 20000 | 10800 | 6200 | 2600 |
| Sample M | 152000 | 80000 | 39600 | 20800 | 12000 | 8000 | 3950 |

Having described the invention in detail and by reference to the preferred embodiments thereof, it will be apparent that modifications and variations are possible without departing from the scope of the appended claims.

What is claimed is:

1. A blend composition comprising about 1 to about 99 parts of one or more cationic polysaccharides and about 99 to about 1 parts of one or more anionic polysaccharides wherein at least one of said anionic polysachharides contains one or more sulfonate groups.

2. The composition according to claim 1 wherein each of said one or more cationic polysaccharides and said one or more anionic polysaccharides are polygalactomannans having a degree of substitution of between about 0.01 and about 3.00.

3. The composition according to claim 2 wherein each of said one or more cationic polygalactomannans and said one or more anionic polygalactomannans are derived from guar gum or locust bean gum.

4. The composition according to claim 3 wherein each of said one or more cationic polygalactomannans and said one or more anionic polygalactomannans are derived from guar gum.

5. The composition according to claim 4 wherein the said one or more cationic polygalactomannans and said one or more anionic polygalactomannans are each separately distributed in a solvent to form solutions which are then mixed together.

6. The composition according to claim 2 wherein said cationic groups of said cationic polygalactomannan are selected from the group consisting of quaternary ammonium groups, acid salts of primary, secondary, and tertiary amines, sulfonium groups and phosphonium groups and mixtures thereof.

7. The composition according to claim 2 wherein said one or more sulfonated groups of said one or more anionic polygalactomannans are derived from ethylenically unsaturated monomers including one or more sulfonate groups.

8. The composition according to claim 7 wherein said ethylenically unsaturated monomers are selected from the group consisting of 2-acrylamido-2-methylpropane sulfonic acid and 1-allyloxy-2-hydroxypropyl sulfonic acid and salts thereof.

9. The composition according to claim 2 wherein the amount and the degree of subsitution of each of said anionic and cationic polysaccharides is matched such that a charge neutral blend composition is produced.

10. The composition according to claim 1 used in foods, explosives, oil field chemicals, personal care products, paper production, textile fibers, agricultural applications and cosmetics.

11. A process for producing a viscous liquid or gel comprising the step of adding to a solvent about 0.1 parts to about 2.0 parts per 100 parts viscous liquid or gel of a blend composition having a ratio of about 1 to about 99 parts of one or more cationic polysaccharides and about 1 to about 99 parts of one or more anionic polysaccharides wherein at least one of said anionic polysaccharides contains one or more sulfonate groups.

12. The process according to claim 11 wherein said solvent is water.

13. The process according to claim 12 wherein each of said one or more cationic polysaccharides and said one or more anionic polysaccharides are polygalactomannans having a degree of substitution of between about 0.01 and about 3.00.

14. The process according to claim 13 wherein each of said one or more cationic polygalactomannans and said one or more anionic polygalactomannans are derived from guar gum or locust bean gum.

15. The process according to claim 14 wherein each of said one or more cationic polygalactomannans and said one or more anionic polygalactomannans are derived from guar gum.

16. The process according to claim 13 wherein the said one or more cationic polygalactomannans and said one or more anionic polygalactomannans are each separately distributed in a solvent to form solutions which are then mixed together.

17. The process according to claim 13 wherein said cationic groups of said cationic polygalactomannan are selected from the group consisting of quaternary ammonium groups, acid salts of primary, secondary, and tertiary amines, sulfonium groups and phosphonium groups and mixtures thereof.

18. The process according to claim 13 wherein said one or more sulfonated groups of said one or more anionic polygalactomannans are derived from ethylenically unsaturated monomers including one or more sulfonate groups.

19. The process according to claim 18 wherein said ethylenically unsaturated monomers are selected from the group consisting of 2-acrylamido-2-methylpropane sulfonic acid and 1-allyloxy-2-hydroxypropyl sulfonic acid and salts thereof.

20. The process according to claim 12 wherein the amount and the degree of subsitution of each of said anionic and cationic polysaccharides is matched such that a charge neutral blend composition is produced.

21. A food, explosive, personal care product, paper production chemical, oil field chemical, textile fiber, agricultural chemical or cosmetic including an amount of a blend composition having a ratio of about 1 to about 99 parts of one or more cationic polysaccharides and about 99 to about 1 parts of one or more anionic polysaccharides wherein at least one of said anionic polysaccharides contains one or more sulfonate groups.

* * * * *